(12) United States Patent
Singh et al.

(10) Patent No.: US 12,396,735 B2
(45) Date of Patent: Aug. 26, 2025

(54) REPOSITIONABLE OVER THE SCOPE CLIP

(71) Applicants: BOSTON SCIENTIFIC MEDICAL DEVICE LIMITED, Galway (IE); BOSTON SCIENTIFIC SCIMED, INC., Maple Grove, MN (US)

(72) Inventors: Rajivkumar Singh, Thane (IN); Deepak Kumar Sharma, Muzaffarnagar (IN); Paul Smith, Smithfield, RI (US); Sharath Kumar G, Kanakapura (IN); Arun Adhikarath Balan, Aluva (IN)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 446 days.

(21) Appl. No.: 18/050,359

(22) Filed: Oct. 27, 2022

(65) Prior Publication Data
US 2023/0181195 A1     Jun. 15, 2023

Related U.S. Application Data

(60) Provisional application No. 63/265,178, filed on Dec. 9, 2021.

(51) Int. Cl.
*A61B 17/128* (2006.01)
*A61B 17/00* (2006.01)

(52) U.S. Cl.
CPC .............. *A61B 17/1285* (2013.01); *A61B 2017/00477* (2013.01); *A61B 2017/00818* (2013.01)

(58) Field of Classification Search
CPC ... A61B 17/1285; A61B 17/10; A61B 17/083; A61B 2017/00477; A61B 2017/00818; A61B 2017/00296
See application file for complete search history.

(56) References Cited

U.S. PATENT DOCUMENTS

| | | | | |
|---|---|---|---|---|
| 5,487,732 | A * | 1/1996 | Jeffrey | A61M 5/3234 604/218 |
| 2005/0049618 | A1 | 3/2005 | Masuda et al. | |
| 2020/0397445 | A1 | 12/2020 | Shikhman et al. | |

FOREIGN PATENT DOCUMENTS

| | | |
|---|---|---|
| EP | 2 316 351 | 5/2011 |
| WO | 2019/135958 | 7/2019 |
| WO | 2022/251771 A1 | 12/2022 |

* cited by examiner

*Primary Examiner* — Brooke Labranche
(74) *Attorney, Agent, or Firm* — Fay Kaplun & Marcin, LLP

(57) ABSTRACT

A clipping system includes an adapter, a clip and an extending member. The adapter mounted over an insertion device. The clip mounted over the adapter and includes first and second jaws connected to one another such that the jaws are movable between an insertion configuration and an initial deployed configuration. The first jaw includes a keyhole opening. The member coupled to the clip and adapter. The member includes a distal end releasably engaging the opening. The distal end has a width smaller than a width of a first portion of the opening and larger than a second portion of the opening so that, when a portion of the member proximal of the distal end is received within the second portion, the adapter is released from the clip while the member remains coupled to the clip. The member forces the clip open as the clip retracts over the adapter.

17 Claims, 5 Drawing Sheets

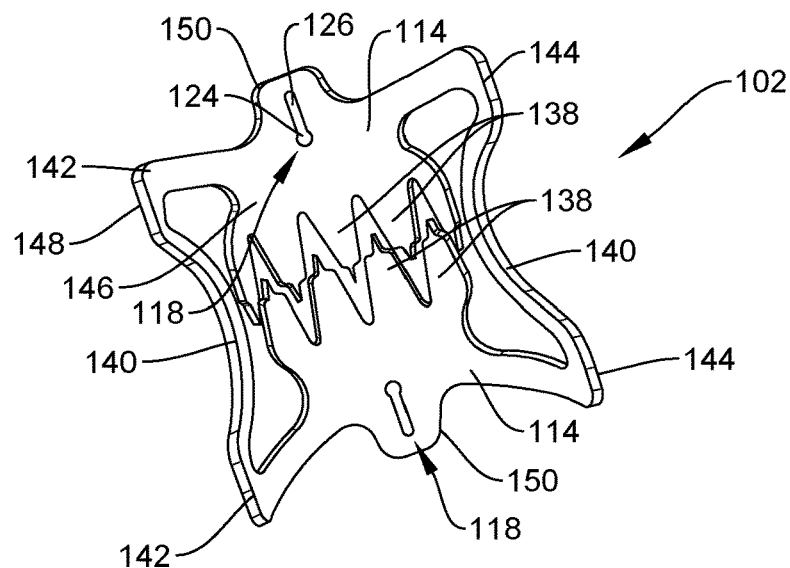
FIG. 3
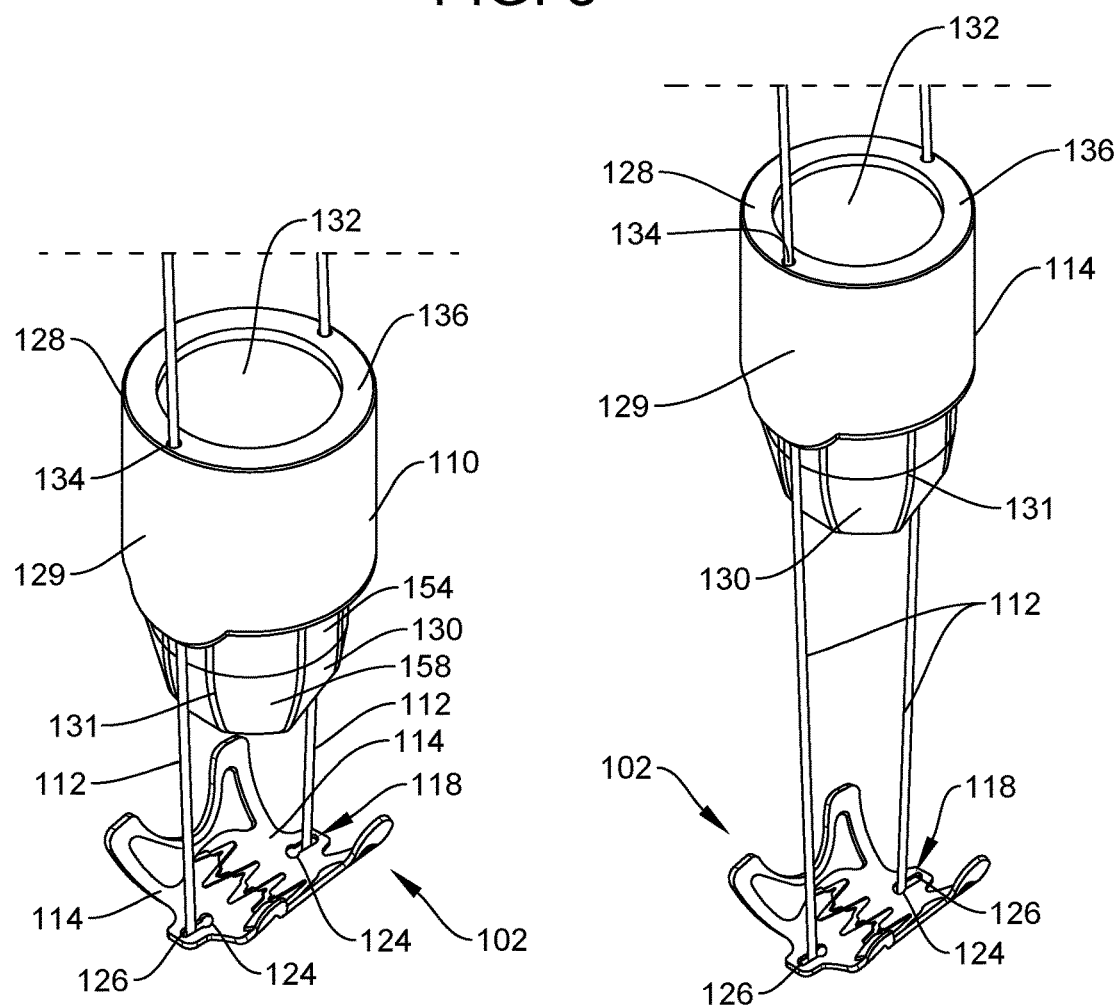
FIG. 4
FIG. 5

REPOSITIONABLE OVER THE SCOPE CLIP

PRIORITY CLAIM

The present disclosure claims priority to U.S. Provisional Patent Application Ser. No. 63/265,178 filed Dec. 9, 2021; the disclosure of which is incorporated herewith by reference.

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks).

Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient. In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue may determine that the distal end of the device and the clip are in a desired position relative to the target tissue. Based on the observation of the target tissue, the operator then deploys the clip without being able to see the clip itself until it is deployed. Once deployed, such current over-the scope clips are generally incapable of being repositioned.

SUMMARY

The present disclosure relates to a clipping system for treating tissue. The system includes an adapter including a proximal portion configured to be mounted over a distal end of an insertion device and a distal portion extending distally from the proximal portion. The system also includes a clip configured to be mounted over the distal portion of the adapter. The clip includes first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween. The first and second jaws are biased toward the initial deployed configuration and the first jaw including a keyhole opening extending therethrough.

In addition, the system includes a first extending member configured to be releasably coupled to the clip and movably connected to the adapter. The first extending member includes an enlarged distal end configured to releasably engage the keyhole opening of the first jaw. The enlarged distal end has a width which is smaller than a width of a first portion of the keyhole opening and larger than a second portion of the keyhole opening so that, when a portion of the first extending member proximal of the enlarged distal end is received within the second portion, the first extending member is engaged therewithin to permit the withdrawal of the adapter proximally away from the clip while the first extending member remains coupled to the clip to place the system in a review configuration in which the clip is physically separated from the adapter to enhance visual observation of the clip. The first extending member is operable to retract the clip proximally over the adapter so that the clip is forced open as the clip is retracted over the adapter freeing the clip from tissue on which it had been clipper.

In an embodiment, the proximal portion of the adapter includes a first hole extending longitudinally through a wall thereof to slidably receive the first extending member therein, the first hole extending through the wall along a axis that is angled with respect to a longitudinal axis of the adapter so that a distal movement of the first extending member relative to the adapter moves the enlarged distal end in a lateral direction relative to the longitudinal axis of the adapter.

In an embodiment, the axis of the first hole intersects the longitudinal axis of the adapter at a point distal of a distal end of the adapter so that, when the first extending member is moved distally relative to the adapter, the enlarged distal end is moved in an inward lateral direction toward the longitudinal axis of the adapter.

In an embodiment, the second portion of the keyhole extends from the first portion toward an exterior edge of the first jaw.

In an embodiment, the enlarged distal end of the first extending member is ball shaped.

In an embodiment, the first portion of the keyhole is substantially circular and the second portion of the keyhole is slotted.

In an embodiment, the system further includes a second extending member configured to be releasably coupled to the second jaw of the clip via a keyhole opening extending through the second jaw, the second extending member including an enlarged distal end configured to releasably engage the keyhole opening of the second jaw, the enlarged distal end of the second extending member having a width that is smaller than a width of a first portion of the keyhole opening of the second jaw and larger than a second portion of the keyhole opening of the second jaw.

In an embodiment, the adapter includes a second hole extending longitudinally through the wall thereof to slidably receive the second extending member therein, the second hole extending through the wall along a axis that is angled with respect to the longitudinal axis of the adapter so that a distal movement of the second extending member relative to the adapter moves the enlarged distal end in a lateral direction relative to the longitudinal axis of the adapter.

In addition, the present disclosure relates to a clipping system for treating tissue which includes an endoscope extending longitudinally from a proximal end to a distal end.

The system also includes an adapter including a proximal portion and a distal portion, the proximal portion configured to be mounted over the distal end of the endoscope so that a channel of the adapter is aligned with a channel of the endoscope. Furthermore, the system includes a clip configured to be mounted over the distal portion of the adapter, the clip including first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween, the first and second jaws being biased toward the initial deployed configuration, each of the first and second jaws including a keyhole opening extending therethrough.

The system further includes first and second extending members configured to be releasably coupled to the clip and movably connected to the adapter, each of the first and second extending members extending from a proximal end accessible a user to an enlarged distal end configured to releasably engage the keyhole opening of a corresponding one of the first and second jaws, the enlarged distal end of each of the first and second extending members having a width which is smaller than a width of a first portion of the keyhole opening of the corresponding one of the first and second jaws and larger than a second portion of the keyhole opening of the corresponding one of the first and second jaws so that, when a portion of the first and second extending members proximal of the enlarged distal ends is received within the second portion of the keyhole openings, the first and second extending members engage the clip so that a longitudinal movement of the first and second extending members relative to the endoscope moves the clip between the insertion configuration, the initial deployed configuration and a review configuration in which the clip is physically separated from the adapter to enhance visual observation of the clip.

In an embodiment, the proximal portion of the adapter includes first and second holes extending longitudinally through a wall thereof to slidably receive the first and second extending members, respectively, therein, each of the first and second holes extending through the wall along a axis that is angled with respect to a longitudinal axis of the adapter so that a distal movement of the first and second extending members relative to the adapter moves the enlarged distal ends of the first and second extending members in a lateral direction relative to the longitudinal axis of the adapter.

In an embodiment, central axes of the first and second holes intersect the longitudinal axis of the adapter distally of the adapter so that, when the first and second extending members are moved distally relative to the adapter, the enlarged distal ends are moved laterally inward toward the longitudinal axis of the adapter.

In an embodiment, the second portion of each of the keyholes extends from the first toward an exterior edge of a corresponding one of the jaws.

In an embodiment, the system further includes first and second outer shafts extending along the endoscope and configured to slidably receive the first and second extending members, respectively, therein, each of the first and second outer shafts extending from a proximal end to a distal end attached to the adapter in alignment with a corresponding one of the first and second holes.

In an embodiment, the system further includes a user interface connected to the proximal ends of the first and second outer shafts and the proximal ends of the first and second extending members.

In an embodiment, the user interface includes a handle member and a spool slidably mounted thereover, the handle member attached to the proximal end of the first and second outer shafts and the spool connected to the proximal ends of the first and second extending member so that a longitudinal movement of the spool relative to the handle member correspondingly moves the clip relative to the endoscope.

In addition, the present disclosure relates to a method for treating tissue. The method includes comprising: inserting a clip to a target area in a body lumen via an endoscope, the clip mounted over a distal end of the endoscope, via an adapter, in an open insertion configuration in which jaws of the clip are separated from one another; drawing tissue into a channel of the adapter and between jaws of the clip; moving the clip from the open insertion configuration toward an initial deployed configuration by releasing a tension along extending members coupled to the clip so that the jaws revert to a biased closed configuration, in which the jaws extend toward one another to grip the tissue received therebetween, the extending members releasably coupled to the clip via enlarged distal ends releasably engaged to keyhole openings extending through each of the jaws, the enlarged distal end of each of the extending members having a width smaller than a first portion of a corresponding one of the keyhole openings and larger than a second portion of the corresponding one of the keyhole openings; and drawing the endoscope proximally away from the clip, while the extending members remain coupled to the clip, toward a review configuration in which a visualization of the clip via the endoscope is enhanced.

In an embodiment, when it is determined that the clip requires repositioning, moving the extending members proximally relative to the endoscope until the clip is drawn proximally over the adapter toward the open insertion configuration and repositioning the clip over the target tissue.

In an embodiment, the method further includes moving the clip from the review configuration toward a final deployed configuration by moving the extending members distally through holes extending through the adapter, the holes extending through the adapter along central axes angled with respect to a longitudinal axis of the adapter so that, moving the extending members distally relative to the adapter causes the enlarged distal ends thereof to be moved laterally relative to the longitudinal axis of the adapter to disengage the extending members from the keyhole openings.

In an embodiment, during movement of the clip from the review configuration toward the final deployed configuration, each of the extending members are moved from the second portion toward the first portion of a corresponding one of the keyholes so that the enlarged distal end is passed proximally through the first portion to release the clip.

In an embodiment, during movement of the clip from the review configuration toward the final deployed configuration, the enlarged distal ends of the extending members are moved laterally inward toward one another to disengage the enlarged distal ends from the keyhole openings.

BRIEF DESCRIPTION

FIG. 3 shows a perspective view of a clip according to the system of FIG. 1;

FIG. 4 shows an adapter and a clip during a movement of the clip between an initial deployed configuration and a review configuration according to the system of FIG. 1;

FIG. 5 shows the adapter and the clip during a movement of the system from the review configuration toward a final deployed configuration;

DETAILED DESCRIPTION

Figure 1:
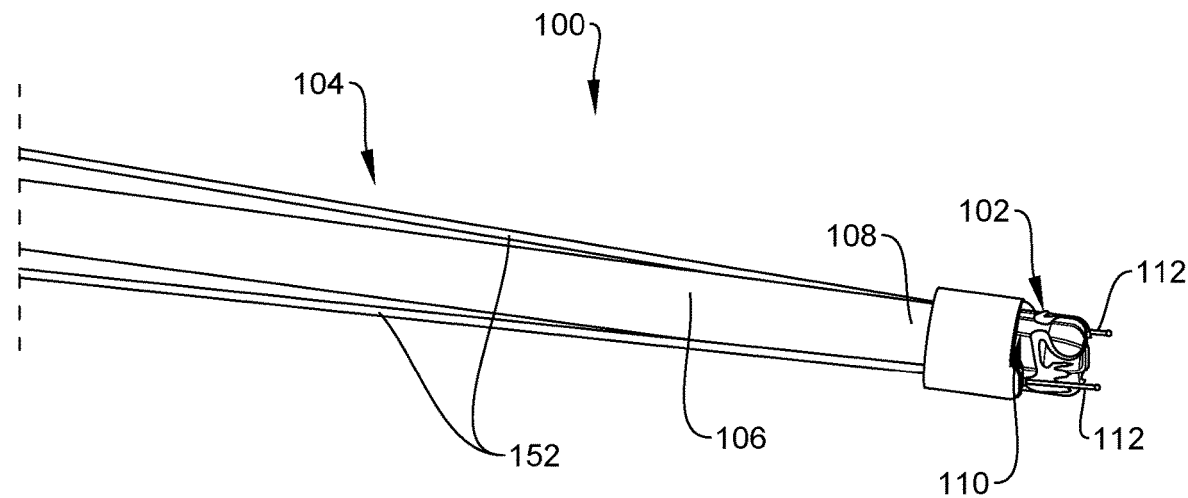
FIG. 1 shows a perspective view of a distal portion of a system according to an exemplary embodiment of the present disclosure.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a final deployment thereof. Exemplary embodiments of the present disclosure comprise a clip mountable over a distal end of an endoscope via an adapter and releasably coupled to extending members so that the clip may be moved between an insertion configuration, an initial deployed configuration, and a review configuration, in which the clip can be viewed prior to being finally deployed.

According to an exemplary embodiment, each of the extending members include an enlarged distal end configured to be releasably coupled to a keyhole shaped opening extending through a portion of a corresponding one of the jaws. The enlarged distal ends of each of the extending members is smaller than a first portion of the keyhole opening but larger than a second portion of the keyhole opening so that the enlarged distal end may be inserted distally through the first portion and moved laterally into the second portion so that a portion of the extending member proximal of the enlarged distal end engages the second portion of the keyhole. While the extending members are engaged with the keyholes of the clip, the extending members may be moved longitudinally relative to the endoscope to move the clip between the insertion configuration, the initial deployed configuration and the review configuration.

In the insertion configuration, the clip is mounted with jaws spread open over the adapter in a proximal position maintained in the insertion configuration ready to receive tissue between jaws thereof while the clip's position minimizes its occlusion of the field of view of the endoscopic vision system. The insertion configuration is configured to facilitate insertion of the endoscope to a target site adjacent to tissue to be clipped while the system allows the clip to be deployed and clipped over tissue in an initial deployed configuration. The device permits the endoscope to be withdrawn proximally away from the clip and the tissue over which it is clipped while the clip remains coupled to the device in a review configuration.

As the endoscope is withdrawn proximally while the clip remains in place over the target tissue, the field of view of the vision system of the endoscope widens to show the clip and the tissue clipped thereby so that the operator can determine whether the position of the clip is desirable or in need of adjustment. If the operator determines that the clip is positioned as desired, the clip is deployed by releasing the clip from the hooked distal of the extending members and left in place clipped over the target tissue. If the operator determines that the position of the clip needs adjustment, the endoscope and the adapter coupled thereto are moved distally to a position adjacent to the clip. The clip is then drawn proximally over the adapter to reopen the clip which is drawn proximally over the distal end of the adapter forcing the clip to open against its natural bias as the clip slides proximally back over the adapter to return to the insertion configuration. After the clip has been removed from the tissue and returned to the insertion configuration, the operator can re-position the endoscope and device as desired, draw target tissue into the adapter (e.g., under suction or a grasper applied via a working channel of the endoscope) and once more deploy the clip from the adapter over the target tissue in the initial deployed position.

The endoscope is then withdrawn proximally once again as the clip remains coupled to the device so that the device moves again into the review configuration. The position of the clip and the clipped tissue are again observed and, this process may be repeated until the clip is positioned as desired. When the operator sees that the tissue over which the clip is closed is the desired portion of tissue, the clip may be deployed and released from the device and endoscope by moving each of the extending members toward the first portion of the keyhole so that the enlarged distal end of each extending members may be released from the clip by being moved proximally through the first portion of the keyhole, as described below. It will be understood by those of skill in the art that terms proximal and distal, as used herein, are intended to refer to a direction toward and away from, respectively, a user of the device.

As shown in FIGS. 1-10, a clipping system 100 for treating tissue defects and/or perforations according to an exemplary embodiment comprises a clip 102 configured to be inserted through, for example, a body lumen to a target area to clip a target tissue thereof. The clip 102 is insertable to the target area via an insertion device 104 which may be, for example, a flexible endoscope 106. As shown in FIGS. 1-5, the clip 102 is coupled to a distal end 108 of the endoscope 106 via an adapter 110 mounted over the distal end 108 of the endoscope 106 and is movable relative to the endoscope 106 via extending members 112, to which the clip 102 is releasably coupled. Each of the extending members 112 includes an enlarged distal end 116 that is configured to be releasably engaged with a portion of a corresponding one of the jaws 114 of the clip 102 to facilitate movement of the clip 102 relative to the endoscope 106 between an insertion configuration (e.g., FIG. 2), an initial deployed configuration (e.g., FIG. 4), a review configuration (e.g., FIG. 4), and a final deployed configuration (e.g., FIG. 5).

According to one embodiment, the enlarged distal end 116 of each of the extending members 112 is configured to releasably engage an opening 118 (e.g., a key-hole shaped opening) extending through a corresponding one of the jaws 114. In particular, as will be described in further detail below, the enlarged end 116 is insertable through a first portion 124 of the opening 118 and engageable with a second portion 126 of the opening 118 so that movement of the extending members 112 relative to the endoscope 106 correspondingly moves the clip 102 relative to the endoscope 106. In the insertion configuration, the clip 102 is mounted over the adapter 110 with jaws 114 separated from one another to receive tissue therebetween. To move the clip 102 from the insertion configuration toward the initial deployed configuration, the extending members 112 are moved distally relative to the endoscope 106, moving the clip 102 distally over and off of the adapter 110 to a closed configuration, in which the jaw 114 move toward one another to grip tissue that has been drawn into the adapter 110 between the jaws 114 when the jaws were in the insertion configuration.

When tissue has been clipped by the jaws 114 in the initial deployed configuration, the clip 102 may then be moved toward the review configuration by moving the extending members 112 further distally away from the endoscope 106 (or drawing the endoscope 106 proximally relative to the extending members 112) so that the clip 102 moved further from the distal end of the adapter 110, while remaining tethered to the insertion device 104 via the extending members 112. This widens the field of view of the endoscope vision system relative to the clip 102 and the tissue clipped thereby and allows for movement and/or angling of the endoscope 106 relative to the clip 102 to enable more extensive observation of the placement and/or position of the clip 102 relative to the target tissue from different angles, etc. As described below, if the user determines the position of the clip 102 is incorrect or sub-optimal, the user may move the endoscope 106 distally to a position adjacent to the clip 102 and then retract the clip 102 back over the distal end of the adapter 110 toward the open insertion configuration by drawing the extending members 112 proximally relative to the adapter 110.

The user may then reposition the endoscope 106 and the clip 102 and repeat these steps so that the placement and/or position of the clip 102 relative to a target tissue may be adjusted, as desired, until a desired position of the clip 102 clipped over a target portion of tissue is achieved. That is, when the operator determines in the review configuration that the clip 102 is not positioned as desired, the clip 102 may be re-opened and removed from the clipped tissue so that the device can be re-positioned until the clip 102 is closed over the desired portion of tissue as desired. Once it is determined that the clip 102 has been clipped over the desired tissue, the enlarged distal end 116 of each of the extending members 112 is laterally relative to the clip 102 (i.e., transverse to a proximal-distal direction) so that the extending members 112 no longer extend through the second portion 126 of the opening 118, but pass through the first portion 124 of the opening 118.

As can be seen in FIG. 3, the first portion 124 of the opening 118 is wider than the second portion 126 so that the enlarged distal end 116 can pass through the first portion 124 to separate the extending members 112 from the clip 102 while the narrower second portion 126 of the opening 118 is sized to prevent the enlarged distal member 116 from passing therethrough. Removing the enlarged distal ends 116 from the openings 118 disengages the clip 102 from the device so that the device and the endoscope may be withdrawn from the body leaving the clip 102 in the body clipped over the target tissue. As will be understood by those of skill in the art and as will be described in further detail below, movement of the clip 102 between the insertion configuration, the initial deployed configuration, the review configuration and the final deployed configuration may be controlled via a user interface 120 which, in one embodiment, as shown in FIGS. 6-9, is coupled proximal ends 150 of the extending members 112.

The clip 102 includes a pair of jaws 114, with a first end 142 of one of the jaws 114 being connected to the first end 142 of the other jaw 114 via a first hinge 140 and a second end 144 of the one jaw 114 connected the second end 144 of the other jaw 114 via a second hinge 140. In one embodiment, each of the jaws 114 extends along a curve from the first end 142 to the second end 144. In one embodiment, the hinges 140 have a natural bias (e.g., a spring bias), biasing the jaws 114 toward the initial deployed configuration in which the jaws 114 are moved toward one another, in a closed configuration to clip tissue received therebetween. Either or both of the jaws 114 may include gripping features. If both jaws 114 have such gripping features 138 such as, for example, teeth, in the initial deployed configuration, the gripping features 138 of one of the jaws 114 contact the gripping features 138 of the other jaw 114. In particular, in the initial deployed configuration, the jaws 114 are moved toward one another to grip tissue received therebetween via the gripping features 138. However, when the clip 102 is mounted over the adapter 110 in the insertion configuration, the jaws 114 extend about opposing portions of the adapter 110 so that an exterior surface 122 of the adapter 110 maintains the clip 102 open with the jaws 114 separated from one another. Thus, when the clip 102 is mounted over the adapter 110 the jaws 114 are spread apart from one another so that tissue drawn into the adapter is received between the jaws 114.

Tissue to be clipped is held within the adapter 110 as the clip 102 is moved distally off of the adapter 110. This frees the jaws 114 to close under the natural bias of the hinges 140 clipping the tissue drawn into the adapter 110. It will be understood by those of skill in the art that the hinges 140 and/or jaws 114 of the clips 102 may be formed of any of a variety of materials so long as the hinges 140 bias the jaws 114 toward the initial deployed configuration, as described above, and so that the bias is sufficiently strong to maintain the clip 102 clipped over target tissue after the clip 102 has been finally deployed (e.g., until edges of an opening in tissue drawn together by the clip 102 have healed together). In one example, portions of the clip 102 (e.g., the hinges 140) are formed of a shape memory alloy such as, for example, Nitinol to provide and/or add to the bias toward the closed configuration.

According to an exemplary embodiment, as described above and as shown in FIG. 3, each of the openings 118 extends through the corresponding jaw 114 from a first surface 146 of the clip 102 which, in the insertion configuration, faces the adapter 110, to a second surface 148 of the clip 102 which faces away from the adapter 110 in the insertion configuration. In one embodiment, each opening 118 extends through the corresponding jaw 114, midway between the first and second ends 142, 144 thereof, so that the openings 118 are opposite one another (e.g., extending through diametrically opposed portions of the clip 102).

As indicated above first portion 124 of each opening 118 is open to the second portion 126 so that the extending members 112 can be slid laterally through the openings 118 from the second portion 126 to the first portion 124. The first portion 124 is sized and shaped to permit a passage of the enlarged distal end 116 of a corresponding one of the extending members 112 therethrough. The second portion 126 is smaller and shaped so that, if the enlarged distal end 116 has been passed through the first portion 124 and the extending member 112 is slid from the first portion 124 to the second portion 126, the enlarged distal end 116 is engaged with the portions of the jaw 114 surrounding the second portion 126 preventing the extending member 112 from being withdrawn from the opening 118. Thus, the enlarged distal end 116 will engage the second portion 126 (e.g., abutting the second surface 148), when proximal tension is applied along the extending member 112.

In one embodiment, the enlarged distal end 116 and the first portion 124 of the opening 118 are circular with a diameter of the first portion 124 larger than that of the enlarged distal end 116. In this embodiment, the second portion 126 is configured as an elongated slot having a width smaller than a diameter of the enlarged distal end 116. It will be understood by those of skill in the art, however, that the opening 118 may have any of a variety of shapes and sizes so long as the key-shaped opening 118 includes a first portion 124 sized, shaped and configured to permit passage of the enlarged distal end 116 therethrough and a second portion 126 sized, shaped and configured to prevent passage of the enlarged distal end 116 therethrough.

In one embodiment, the second portion 126 of the opening 118 extends from the first portion 124 toward an exterior edge of the jaw 114 (away from the gripping features 138). Thus, according to an exemplary embodiment, the extending members 112 are released from the clip 102 by moving the extending members 112 and the enlarged distal ends 116 through the second portions 126 laterally inward toward a longitudinal axis of the endoscope 106 until the enlarged distal ends 116 reach the first portions 124. Once the extending members 112 extend through the first portions 124, the enlarged distal ends 116 are drawn proximally through the first portions 124 of the openings 118 so that the extending members 112 are released from the clip 102.

It will be understood by those of skill in the art, however, that the opening 118 may have any of a variety of orientations relative to each of the jaws 114, so long as the orientation of the opening 118 extending through each of the jaws 114 corresponds to a configured movement of a corresponding one of the extending members 112 relative to the clip 102 during movement of the system 100 from the review configuration toward the final deployed configuration. For example, where one or more of the distal ends 116 of the extending members 112 is configured to be moved laterally outward relative to the longitudinal axis of the endoscope 106, a corresponding one of the opening 118 will include a second portion 126 extending from the first portion 124 toward a side of the corresponding one of the jaws 114 including the gripping features 138. Those skilled in the art will understand also that the openings 118 may be configured differently from one another so long as the user can manipulate the extending members 112 so that the enlarged distal ends are simultaneously or serially movable into the first portions 124 of the openings 118 when it is desired to finally deploy the clip 102.

Figure 2:
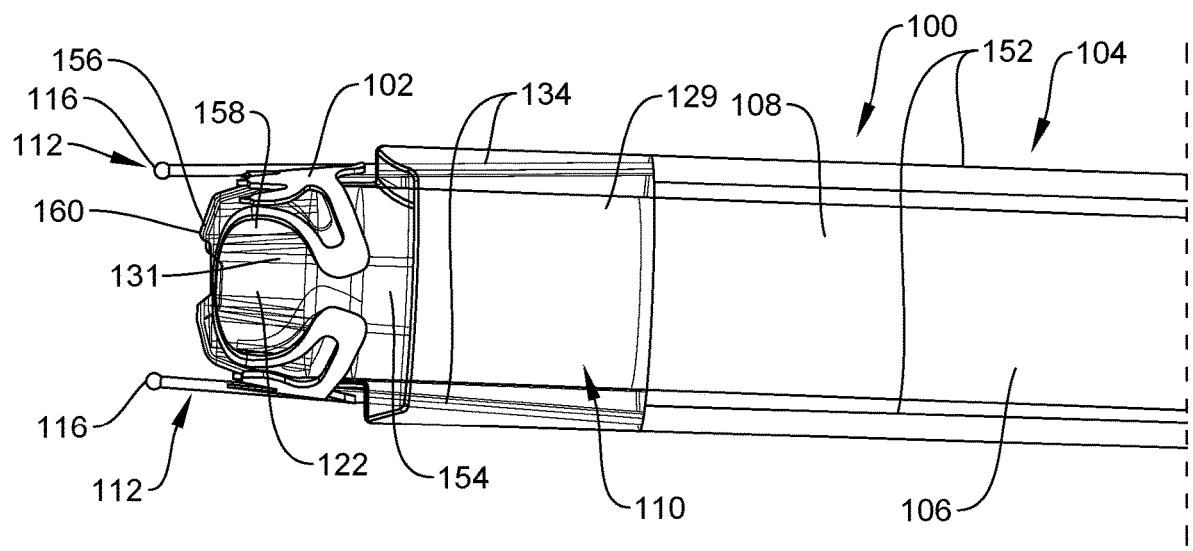
FIG. 2 shows a partially transparent longitudinal side view of a distal end of the system according to FIG. 1.
Figure 6:
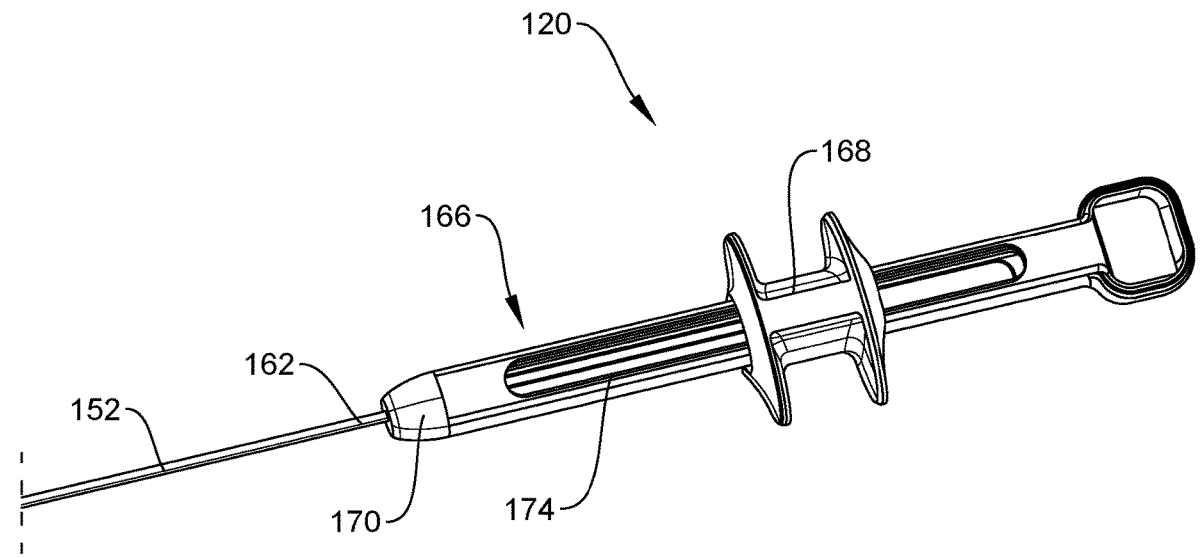
FIG. 6 shows a perspective view of a user interface according to the exemplary embodiment shown in FIG. 1.
Figure 7:
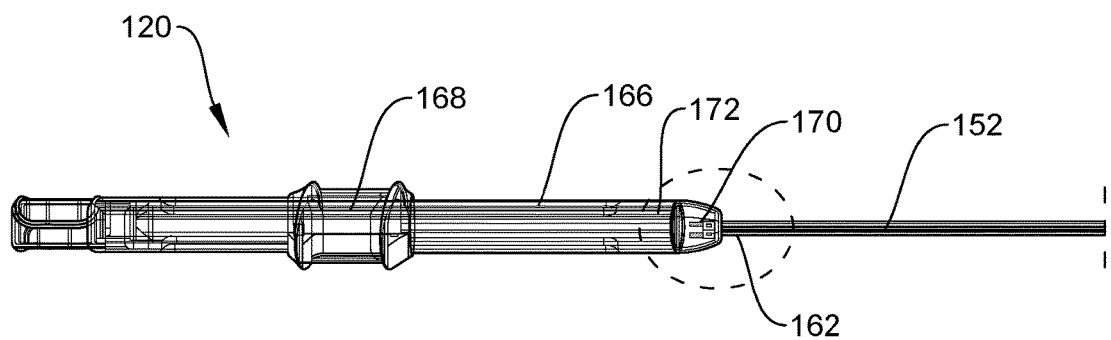
FIG. 7 shows transparent longitudinal side view of the user interface according to the system of FIG. 1.
Figure 8:
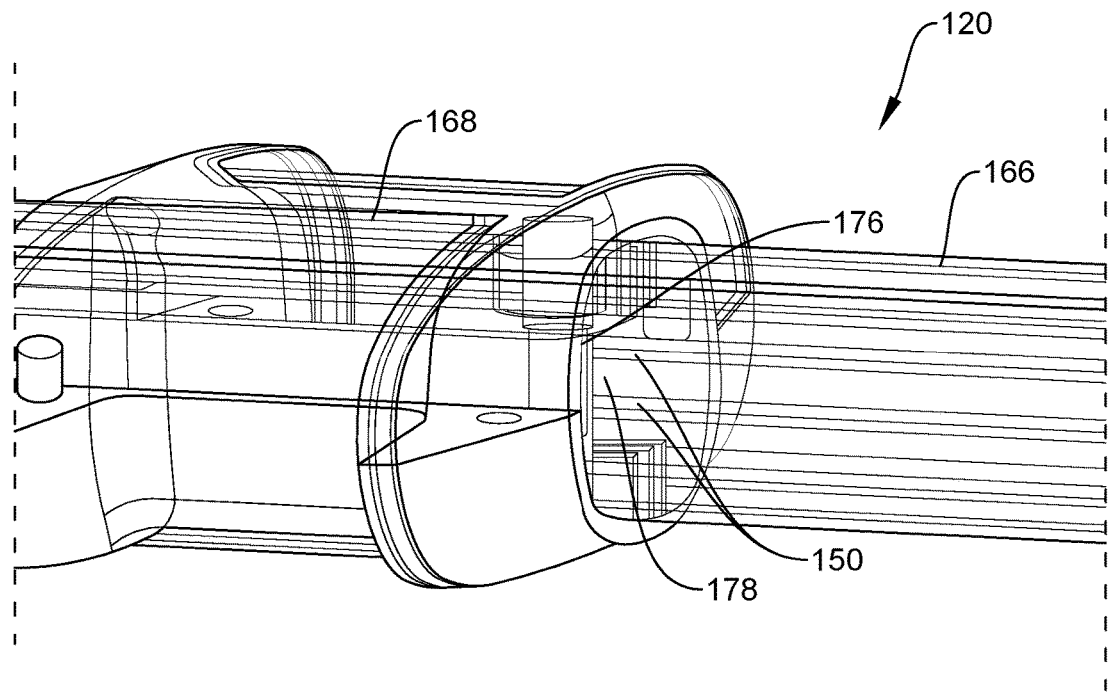
FIG. 8 shows an enlarged transparent, perspective view of the user interface of the system of FIG. 1.
Figure 9:
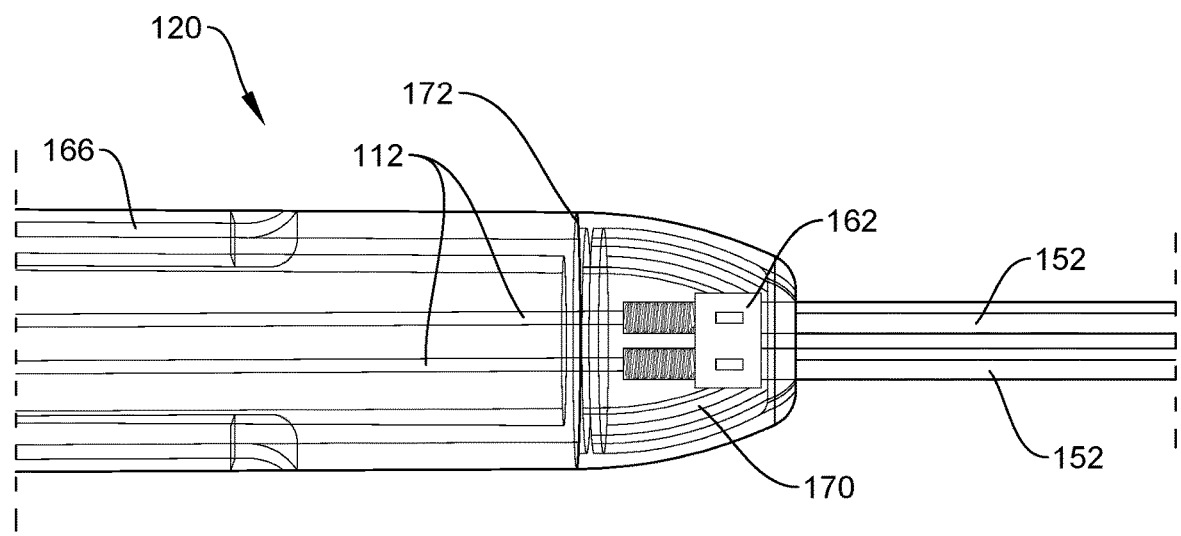
FIG. 9 shows an enlarged transparent, longitudinal side view of the user interface according to the system of FIG. 1.

As discussed above, the clip 102 may be mounted to the insertion device 104, as shown in FIGS. 1 and 2, which may include any standard endoscope 106. The clip 102 may be mounted to the endoscope 106 via the adapter 110, which is sized, shaped and configured to be mounted over the distal end 108 of the endoscope 106 or any other desired insertion device. As will be understood by those of skill in the art, the endoscope 106 of this embodiment is configured to be inserted through a body lumen to a target area within the lumen and thus, must be sufficiently flexible to navigate through even tortuous paths of the body lumen. The adapter 110 extends from a proximal end 128 to a distal end 130 and includes a channel 132 extending therethrough to an open distal end through which tissue may be drawn into the channel 132.

A proximal portion 129 of the adapter 110 is configured to be mounted over the distal end 108 of the endoscope 106 while a distal portion 131 of the adapter is configured to receive the clip 102 thereover in the insertion configuration. The proximal portion 129 of the adapter 110 may be mounted to the endoscope 106 via, for example, a friction fit, so that the channel 132 of the adapter 110 is substantially longitudinally aligned with a longitudinal axis of the endoscope 106 open to a working channel of the endoscope (e.g., so that suction or a grasper may be inserted therethrough to draw tissue into the channel 132) and permitting a vision system of the endoscope 106 to visualize the clip 102 and any tissue clipped or to be clipped thereby. In another embodiment, to enhance the visibility of the tissue and/or the clip 102, the adapter 110 may be formed of a transparent material.

In one embodiment, the proximal portion 129 of the adapter 110 of this embodiment includes a pair of holes 134 extending longitudinally through a wall 136 thereof. Each of the holes 134 is configured to slidably receive a corresponding one of the extending members 112. As will be described in further detail below, the extending members 112 are received within the holes 134 so that distal ends 116 extend distally from the holes 134 to be coupled to the clip 102, which, in the insertion configuration, is mounted over the distal portion 131 of the adapter 110. According to an exemplary embodiment, each of the holes 134 extends through the wall 136 of the proximal portion 129 along an axis angled with respect to a longitudinal axis of the adapter 110.

In one embodiment, the axes of the holes 134 are angled with respect to the longitudinal axis of the adapter 110 so that the central axes of the holes 134 intersect with the longitudinal axis of the adapter 110 distally of the distal end of the adapter 110. In this embodiment, the holes 134 are angled toward one another from the proximal end 128 of the adapter 110 toward the distal end 130 of the adapter 110. Thus, when the extending members 112 are moved distally through the holes 134, the enlarged distal ends 116 thereof are moved laterally inward, toward one another and toward the longitudinal axis of the endoscope 106. As will be described in further detail below, lateral movement of the enlarged distal ends 116 facilitates release of the clip 102 from the review configuration to the final deployed configuration.

Although the exemplary embodiments show and describe the holes 134 extending along axes which intersect with the longitudinal axis of the adapter 110 (and with one another) distally of the adapter 110, it will be understood by those of skill in the art that the holes 134 may extend through the adapter 110 at any of a variety of angles relative to the longitudinal axis of the adapter 110 so long as the holes 134 angle the extending members 112 in such a way as to permit the enlarged distal ends 116 to be moved in laterally relative to the endoscope 106 to facilitate release of the enlarged distal ends 116 from the openings 118 of the clip 102 (e.g., as the extending members 112 are moved distally relative to the adapter 110 and the clip 102). For example, in another embodiment, axes of the holes 134 intersect with the longitudinal axis of the adapter 110 proximally of the adapter 110. In yet another embodiment, an axis of a first one of the holes 134 intersects with the longitudinal axis of the adapter 110 distally of the adapter 110 while a axis of a second one of the pair of holes 134 intersects with the longitudinal axis of the adapter 110 proximally thereof.

An outer diameter of the distal portion 131 of the adapter 110 is sized, shaped and configured to receive the clip 102 thereover, in the insertion configuration. In one exemplary embodiment, the distal portion 131 tapers toward the distal end 130 so that the bias of the clip 102 toward the initial deployed configuration aids in drawing the clip 102 distally over the adapter 110 (i.e., the closing force of the clip 102 draws the clip 102 distally as the jaws 114 slide over the tapered surface of the adapter 110). When the clip 102 is mounted over the distal portion 131 of the adapter 110, with each the jaws 114 spread apart and extending over opposing portions of the adapter 110, an exterior surface of the adapter 110 prevents the jaws 114 from closing (i.e., constrains the clip 102 toward the insertion configuration with the jaws 114 open to receive tissue drawn into the adapter 110).

The clip 102 remains mounted over the adapter 110 in the insertion configuration so long as proximally directed tension applied to the extending members 112 and friction between the clip 102 and the adapter 110 is maintained at a predetermined level. When tension is removed from the extending members 112 and/or a distally directed force is applied to the extending members 112, the natural bias of the clip 102 draws the jaws 114 toward one another and the clip 102 is moved distally over the tapered surface of the adapter 110 until the clip 102 slides distally off of the adapter 110.

The distal portion 131 of the adapter 110 of one embodiment includes a plurality of longitudinally extending flat portions 154 distributed about the circumference of the exterior surface 122 of the adapter 110. Each of the flat portions 154 extends along at least a portion of a length of the distal portion 131 and covers a portion of a perimeter (e.g., circumference) of the distal portion 131. The flat portions 154 which may be equally sized and separated from one another about the circumference of the distal portion 131 provide clearance between portions of the clip 102 and the adapter 110 which reduces friction between the clip 102 and the distal portion 131 of the adapter 110 to facilitate a movement of the clip 102 between the insertion configuration and the initial deployed configuration.

The distal portion 131 of the adapter 110 of this embodiment also includes a plurality of projections 156 extending radially into the channel 132 of the adapter 110. In one embodiment, each of the projections 156 extends from a curved portion 158 of the distal portion 131 extending between adjacent flat portions 154. In one exemplary embodiment, a distal face 160 of each these curved portions 158 is angled with respect to a longitudinal axis of the adapter 110 so that, when the clip 102 is drawn proximally from the initial deployed configuration, the jaws 114 abut the distal face 160 and the angle of these projections 156 facilitates the re-opening of the jaws 114 against their natural bias, so that the clip 102 may be drawn proximally over the adapter 110 opening the jaws 114 and returning the clip 102 to the insertion configuration. That is, the jaws 114 slide proximally over the projections 156 to facilitate the opening of the jaws 114 so that the clip 102 is released from the clipped tissue and slid proximally back onto the adapter 110.

As described above, the insertion device 104 includes extending members 112 extending along a length of the endoscope 106 from proximal ends 150 which remain accessible to the user via, for example, a user interface 120 outside the body, to the enlarged distal ends 116. In one embodiment, the insertion device 104 includes two extending members 112, each which is configured to be releasably coupled to a corresponding one of the jaws 114. In one embodiment, the enlarged distal end 116 may be ball shaped. The ball-shaped enlarged distal end 116 has a diameter larger than a remaining length of the extending member 112 (i.e., a portion of the extending member 112 extending proximally from the enlarged distal end 116).

In this embodiment, the diameter of the ball-shaped distal end 116 is smaller than the diameter of the correspondingly sized and shaped first portion 124 of the opening 118. The width of the second portion 126, is larger than the diameter of the portion of the extending members 112 extending proximally from the enlarged distal ends 116 so that the extending members 112 may be moved through the second portions 126 of the openings 118 to the first portions 124. The width of the second portion 126 is smaller than the diameter of the ball-shaped enlarged distal end 116 so that, when the extending member 112 extends through the second portion 126, as shown in FIG. 4, a remaining length of the extending member 112 proximal of the enlarged distal end 116 is slidable through the second portion 126, while the enlarged distal end 116 is prevented from passing therethrough. Thus, the enlarged distal end 116 engages the second surface 148, releasably engaging the extending member 112 to the jaw 114 of the clip 102.

It will be understood by those of skill in the art that, in the insertion configuration, each of the enlarged distal ends 116 engages a corresponding one of the openings 118 and abuts the second surface 148 of the corresponding jaw 114 while a portion of each of the extending members 112 extending proximally therefrom is held between the exterior surface 122 of the adapter 110 and the corresponding one of the jaws 114. Thus, in the insertion configuration, the extending members 112 are further prevented from being inadvertently disengaged from the clip 102. In an exemplary embodiment, the extending members 112 are formed as flexible strands, filaments or coils formed of, for example, a metal or polymer.

Each extending member 112 in this embodiment extends through, for example, an outer shaft 152 extending along a length of the endoscope 106 from a proximal end 162 connected to a portion of the user interface 120 to a distal end 164 connected to the adapter 110. In particular, the distal ends 164 of the outer shafts 152 are connected to the proximal end 128 of the adapter 110 so that each outer shaft 152 is aligned with a corresponding one of the holes 134 of the adapter 110. Thus, each extending member 112 extends through a corresponding one of the outer shafts 152 and the holes 134 so that the extending member 112 is longitudinally movable therewithin, relative to the endoscope 106, to control movement of the clip 102 relative to the endoscope 106. The outer shafts 152 also reduce interference with movement of the extending members 112 by tissue surrounding the endoscope 106 and protects this tissue from friction or other damage that might occur as the extending members 112 are moved proximally and distally relative to the endoscope 106.

In one embodiment, each of the outer shafts 152 (and the corresponding one of the extending members 112) extends along diametrically opposed portions of the endoscope 106. Each of the outer shafts 152 in this embodiment is substantially longitudinally aligned with one of the holes 134 of the adapter 110 and one of the openings 118 of a corresponding one of the jaws 114 so that, when the clip 102 is mounted over the adapter 110, the enlarged distal ends 116 of the extending members 112 extend distally from the holes 134 of the adapter 110 to releasably engage the jaws 114 of the clip 102. It will be understood by those skilled in the art, however, that any arrangement of the outer shafts 152 may be employed so long as the extending members 112 are slidably housed therein and are delivered to desired locations on the clip 102 as described above.

According to an exemplary embodiment, as shown in FIGS. 6-9, the user interface 120 includes a handle member 166 and a spool 168 slidably mounted thereover. The handle member 166 is connected to the proximal ends 162 of the outer shafts 152 while the spool 168 is connected to the proximal ends 150 of the extending members 112. Thus, moving the spool 168 longitudinally over the handle member 166 correspondingly moves the extending members 112 longitudinally relative to the endoscope 106. Since the clip 102 is releasably coupled to the enlarged distal ends 116 of the extending members 112, the spool 168 may be moved relative to the handle member 166 to move the clip 102 between the insertion configuration, the initial deployed configuration, the review configuration and the final deployed configuration.

In one embodiment, the proximal ends 162 of the outer shafts 152 are connected to the handle member 166 via an end cap 170 attached to a distal end 172 of the handle member 166. Proximal ends 162 may be fixed within the end cap 170 via any of a number of different mechanisms. For example, the proximal ends 162 may be crimp attached, welded or adhered to the end cap 170.

In one embodiment, the spool 168 is slidably mounted over the handle member 166 via an elongated slot 174 extending longitudinally along the handle member 166. The spool 168 includes, for example, a rod 176 extending across a channel 178 of the spool 168, the rod 176 received within the elongated slot 174 to permit a longitudinal slidable movement of the spool 168 relative to the handle member 166. The proximal ends 150 of the extending members 112 are affixed to the rod 176 so that a longitudinal movement of the spool 168 relative to the handle member 166 correspondingly moves the clip 102 relative to the endoscope 106 between the insertion, initial deployed, review and final deployed configurations.

According to an exemplary method for tissue closure utilizing the clipping system 100, the clip 102 may be inserted through a body lumen such as, for example, the GI tract, to a target area within the body lumen via the insertion device 104 which, in one embodiment, may include the endoscope 106. As described above, in the insertion configuration, the clip 102 is mounted to the distal end 108 of the endoscope 106 via the adapter 110, so that the jaws 114 are separated from one another toward the open configuration. The clip 102 is guided to the target area via the visualization system of the endoscope and positioned over a target tissue. A suction force and/or tissue graspers may be applied through a working channel of the endoscope 106 so that the target tissue may be drawn into the channel 132 of the adapter 110. Thus, when the clip 102 is moved toward the initial deployed configuration by releasing a tension along the extending members 112 (e.g., moving the extending members 112 proximally relative to the endoscope 106), the clip 102 slides distally along the adapter 110 toward the biased closed configuration to grip the target tissue.

It will be understood by those of skill in the art that suctioning and/or gripping of the tissue in this initial deployed configuration may obstruct an imaging/optical lens of the endoscope 106 so that the user is unable to visualize and/or confirm whether a desired target tissue has been properly clipped. Thus, as shown in FIG. 4, the clip 102 may be moved toward the review configuration by drawing the endoscope 106 distally relative to the clip 102, while a tension is maintained along the extending members 112 so that the clip 102 remains clipped on the tissue. A distance between the adapter 110 and the clip 102 widens a field of view of the endoscope 106 so that the clip 102, and the tissue gripped thereby, may be viewed via the optical/visualization system of the endoscope 106.

If, upon visualization, the user determines that the clip 102 requires an adjustment and/or a repositioning relative to the target tissue, the extending members 112 may be translated proximally relative to the endoscope 106 until the clip 102 is moved proximally over the adapter 110, as described above, toward the open insertion configuration. As the clip 102 is moved toward the open configuration, the tissue gripped thereby is released, permitting the clip 102 to be repositioned over the target tissue, as desired. The clip 102 may then once again moved toward the initial deployed configuration, and then again toward the review configuration. This process may be repeated, as necessary, until the user is able to visually confirm that the clip 102 has been clipped over the target tissue, as desired.

Once the user confirms that the target tissue has been clipped, as desired, the clip 102 may be moved from the review configuration toward the final deployed configuration, by releasing the clip 102 from the extending members 112. As described above, in one embodiment, the extending members 112 may be moved distally relative to the clip 102 so that the extending members 112 are moved distally through the holes 134 of the adapter 110. As described above, the holes 134 of the adapter 110 are angled with respect to the longitudinal axis of the adapter so that the distal movement of the extending members 112 relative to the adapter 110 moves the enlarged distal ends 116 of the extending member 112 in a lateral direction relative to the clip 102.

In one embodiment, the distal ends 116 are moved laterally toward one another and relative to the clip 102 so that the enlarged distal ends 116 are moved from the second portions 126 of the keyhole openings 118 toward the first portions 124 of the keyhole openings 118, as shown in FIG. 5. The enlarged distal ends 116 are sized and shaped to be smaller than the first portions 124 so that, once they are received within the first portions 124, the extending members 112 (and the insertion device 104) may be withdrawn proximally therefrom to release the clip 102 in the final deployed configuration.

Figure 10:
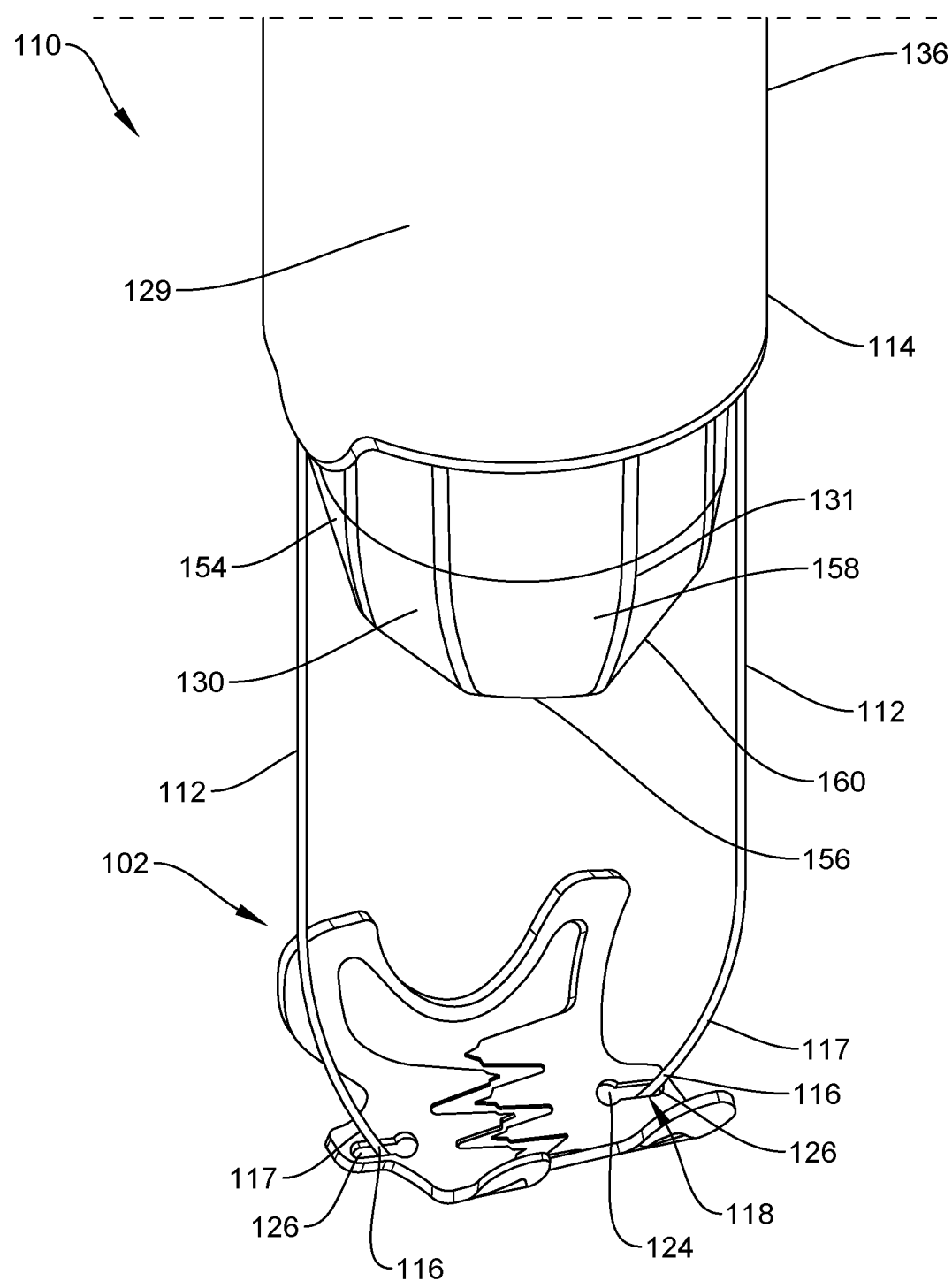
FIG. 10 shows a perspective view of an adapter and a clip according to a further embodiment during movement of the system from a review configuration toward a final deployed configuration.

In one embodiment, each of the distal portions of the extending members 112 includes a bendable portion 117 configured to bend radially inward relative to a longitudinal axis of the channel 132 when a predetermined distal force is applied to the extending member 112. In the initial deployed configuration, as shown in FIG. 4, the extending members 112 and the bendable portions 117 are substantially straight, i.e., the bendable portions 117 extend through the second portions 126 of the keyhole openings 118 and are not bent radially inward relative to the longitudinal axis of the channel 132. Thus, when a user wants to deploy the clip 102 of this embodiment, the extending members 112 are advanced distally to move the clip 102 off the cap 110, as described above, so that the clip 102 closes over target tissue. The user then pushes the extending members 112 distally against the tissue to bend the bendable portions 117 radially inward, as shown in FIG. 10, so that the enlarged distal ends 116 move radially inward through the keyhole openings 118 toward the first portions 124 of the keyhole openings 118. As described and shown with respect to FIG. 5, the enlarged distal ends 116 are sized and shaped to be smaller than the first portions 124 so that, once the enlarged distal ends 116 are received within the first portions 124, the extending members 112 (and the insertion device 104) may be withdrawn proximally therefrom to release the clip 102 from the device 100 so that the clip 102 may be left in the final deployed configuration clipped over target tissue while the rest of the device 100 is withdrawn from the body.

In a further exemplary embodiment, the bendable portions 117 are pre-shaped so that, when not constrained by the holes 134, the bendable portions 117 bend radially inward relative to a longitudinal axis of the channel 132. Thus, when a user wants to deploy the clip 102 of this embodiment, the extending members 112 are advanced distally to move the clip 102 off the cap 110, as described above, so that the clip 102 closes over target tissue and the bendable portions 117, now unconstrained by the holes 134, bend radially inward (i.e., so that the enlarged distal ends 116 move toward one another). The user then pushes the extending members 112 distally against the tissue to further bend the bendable portions 117 radially inward so that the enlarged distal ends 116 move radially inward through the keyhole openings 118 toward the first portions 124 of the keyhole openings 118, as shown in FIG. 10.

In a further exemplary embodiment, only one of the extending members 112 includes a bendable portion 117 as described above, while in another exemplary embodiment, the distal portions of each of the extending members 112 is substantially straight until the enlarged distal ends 116 are pressed distally against the tissue to bend the distal portions of the extending members radially inward to move the enlarged distal ends 116 into the first portions 124 of the keyhole openings 118 in a manner similar to that described above.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A clipping system for treating tissue, comprising:
   an adapter including a proximal portion configured to be mounted over a distal end of an insertion device and a distal portion extending distally from the proximal portion;
   a clip configured to be mounted over the distal portion of the adapter, the clip including first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween, the first and second jaws being biased toward the initial deployed configuration and the first jaw including a keyhole opening extending therethrough; and
   a first extending member configured to be releasably coupled to the clip and movably connected to the adapter, the first extending member including an enlarged distal end configured to releasably engage the keyhole opening of the first jaw, the enlarged distal end having a width which is smaller than a width of a first portion of the keyhole opening and larger than a second portion of the keyhole opening so that, when a portion of the first extending member proximal of the enlarged distal end is received within the second portion, the first extending member is engaged therewithin to permit the withdrawal of the adapter proximally away from the clip while the first extending member remains coupled to the clip to place the system in a review configuration in which the clip is physically separated from the adapter to enhance visual observation of the clip, the first extending member being operable to retract the clip proximally over the adapter so that the clip is forced open as the clip is retracted over the adapter freeing the clip from tissue on which it had been clipped,
   wherein the proximal portion of the adapter includes a first hole extending longitudinally through a wall thereof to slidably receive the first extending member therein, the first hole extending through the wall along an axis that is angled with respect to a longitudinal axis of the adapter so that a distal movement of the first extending member relative to the adapter moves the enlarged distal end in a lateral direction relative to the longitudinal axis of the adapter.

2. The system of claim 1, wherein the axis of the first hole intersects the longitudinal axis of the adapter at a point distal of a distal end of the adapter so that, when the first extending member is moved distally relative to the adapter, the enlarged distal end is moved in an inward lateral direction toward the longitudinal axis of the adapter.

3. The system of claim 2, wherein the second portion of the keyhole extends from the first portion toward an exterior edge of the first jaw.

4. The system of claim 1, wherein the enlarged distal end of the first extending member is ball shaped.

5. The system of claim 4, wherein the first portion of the keyhole is substantially circular and the second portion of the keyhole is slotted.

6. The system of claim 1, further comprising a second extending member configured to be releasably coupled to the second jaw of the clip via a keyhole opening extending through the second jaw, the second extending member including an enlarged distal end configured to releasably engage the keyhole opening of the second jaw, the enlarged distal end of the second extending member having a width that is smaller than a width of a first portion of the keyhole opening of the second jaw and larger than a second portion of the keyhole opening of the second jaw.

7. The system of claim 6, wherein the adapter includes a second hole extending longitudinally through the wall thereof to slidably receive the second extending member therein, the second hole extending through the wall along an axis that is angled with respect to the longitudinal axis of the adapter so that a distal movement of the second extending member relative to the adapter moves the enlarged distal end in a lateral direction relative to the longitudinal axis of the adapter.

8. A clipping system for treating tissue, comprising:
   an endoscope extending longitudinally from a proximal end to a distal end;
   an adapter including a proximal portion and a distal portion, the proximal portion configured to be mounted over the distal end of the endoscope so that a channel of the adapter is aligned with a channel of the endoscope;
   a clip configured to be mounted over the distal portion of the adapter, the clip including first and second jaws connected to one another such that the first and second jaws are movable between an insertion configuration, in which the first and second jaws extend about opposing portions of the distal portion of the adapter and are separated from one another to receive tissue therebetween, and an initial deployed configuration, in which the clip is moved distally off of the adapter so that the first and second jaws are drawn toward one another to grip tissue therebetween, the first and second jaws being biased toward the initial deployed configuration, each of the first and second jaws including a keyhole opening extending therethrough; and first and second extending members configured to be releasably coupled to the clip and movably connected to the adapter, each of the first and second extending members extending from a proximal end accessible a user to an enlarged distal end configured to releasably engage the keyhole opening of a corresponding one of the first and second jaws, the enlarged distal end of each of the first and second extending members having a width which is smaller than a width of a first portion of the keyhole opening of the corresponding one of the first and second jaws and larger than a second portion of the keyhole opening of the corresponding one of the first and second jaws so that, when a portion of the first and second extending members proximal of the enlarged distal ends is received within the second portion of the keyhole openings, the first and second extending members engage the clip so that a longitudinal movement of the first and second extending members relative to the endoscope moves the clip between the insertion configuration, the initial deployed configuration and a review configuration in which the clip is physically separated from the adapter to enhance visual observation of the clip, wherein the proximal portion of the adapter includes first and second holes extending longitudinally through a wall thereof to slidably receive the first and second extending members, respectively, therein, each of the first and second holes extending through the wall along a axis that is angled with respect to a longitudinal axis of the adapter so that a distal movement of the first and second extending members relative to the adapter moves the enlarged distal ends of the first and second extending members in a lateral direction relative to the longitudinal axis of the adapter.

9. The system of claim 8, wherein central axes of the first and second holes intersect the longitudinal axis of the adapter distally of the adapter so that, when the first and second extending members are moved distally relative to the adapter, the enlarged distal ends are moved laterally inward toward the longitudinal axis of the adapter.

10. The system of claim 9, wherein the second portion of each of the keyholes extends from the first toward an exterior edge of a corresponding one of the jaws.

11. The system of claim 8, further comprising first and second outer shafts extending along the endoscope and configured to slidably receive the first and second extending members, respectively, therein, each of the first and second outer shafts extending from a proximal end to a distal end attached to the adapter in alignment with a corresponding one of the first and second holes.

12. The system of claim 11, further comprising a user interface connected to the proximal ends of the first and second outer shafts and the proximal ends of the first and second extending members.

13. The system of claim 12, wherein the user interface includes a handle member and a spool slidably mounted thereover, the handle member attached to the proximal end of the first and second outer shafts and the spool connected to the proximal ends of the first and second extending member so that a longitudinal movement of the spool relative to the handle member correspondingly moves the clip relative to the endoscope.

14. A method for treating tissue, comprising:
inserting a clip to a target area in a body lumen via an endoscope, the clip mounted over a distal end of the endoscope, via an adapter, in an open insertion configuration in which jaws of the clip are separated from one another;
drawing tissue into a channel of the adapter and between jaws of the clip;
moving the clip from the open insertion configuration toward an initial deployed configuration by releasing a tension along extending members coupled to the clip so that the jaws revert to a biased closed configuration, in which the jaws extend toward one another to grip the tissue received therebetween, the extending members releasably coupled to the clip via enlarged distal ends releasably engaged to keyhole openings extending through each of the jaws, the enlarged distal end of each of the extending members having a width smaller than a first portion of a corresponding one of the keyhole openings and larger than a second portion of the corresponding one of the keyhole openings;
drawing the endoscope proximally away from the clip, while the extending members remain coupled to the clip, toward a review configuration in which a visualization of the clip via the endoscope is enhanced; and
moving the clip from the review configuration toward a final deployed configuration by moving the extending members distally through holes extending through the adapter, the holes extending through the adapter along central axes angled with respect to a longitudinal axis of the adapter so that, moving the extending members distally relative to the adapter causes the enlarged distal ends thereof to be moved laterally relative to the longitudinal axis of the adapter to disengage the extending members from the keyhole openings.

15. The method of claim 14, wherein, when it is determined that the clip requires repositioning, moving the extending members proximally relative to the endoscope until the clip is drawn proximally over the adapter toward the open insertion configuration and repositioning the clip over the target tissue.

16. The method of claim 14, wherein, during movement of the clip from the review configuration toward the final deployed configuration, each of the extending members are moved from the second portion toward the first portion of a corresponding one of the keyholes so that the enlarged distal end is passed proximally through the first portion to release the clip.

17. The method of claim 14, wherein, during movement of the clip from the review configuration toward the final deployed configuration, the enlarged distal ends of the extending members are moved laterally inward toward one another to disengage the enlarged distal ends from the keyhole openings.

* * * * *